US008987331B2

(12) United States Patent
Larson et al.

(10) Patent No.: US 8,987,331 B2
(45) Date of Patent: *Mar. 24, 2015

(54) TWO-PART DISINFECTANT SYSTEM AND RELATED METHODS

(71) Applicant: Solutions BioMed, LLC, Orem, UT (US)

(72) Inventors: Brian G. Larson, Alpine, UT (US); Daryl J. Tichy, Orem, UT (US)

(73) Assignee: Solutions BioMed, LLC, Orem, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/269,443

(22) Filed: May 5, 2014

(65) Prior Publication Data
US 2014/0284355 A1   Sep. 25, 2014

Related U.S. Application Data

(63) Continuation of application No. 12/617,521, filed on Nov. 12, 2009, now Pat. No. 8,716,339.

(60) Provisional application No. 61/113,946, filed on Nov. 12, 2008.

(51) Int. Cl.
A61K 31/327   (2006.01)
A01N 59/16    (2006.01)
A01P 1/00     (2006.01)
A01N 37/00    (2006.01)
A61L 2/18     (2006.01)
A01N 31/02    (2006.01)

(52) U.S. Cl.
CPC . A61L 2/18 (2013.01); A01N 31/02 (2013.01); A01N 59/16 (2013.01)
USPC ............................. 514/557; 424/618

(58) Field of Classification Search
CPC ....... A01N 59/16; A01N 59/06; A01N 37/02; A01N 37/06; A01N 25/04
See application file for complete search history.

(56) References Cited

U.S. PATENT DOCUMENTS

| 716,077 | A | 12/1902 | Morrin |
|---|---|---|---|
| 734,467 | A | 7/1903 | Martien |
| 2,103,999 | A | 12/1937 | Muller et al. |
| 2,304,104 | A | 12/1938 | Klabunde et al. |
| 3,156,369 | A | 11/1964 | Bowes et al. |
| 3,172,568 | A | 3/1965 | Modderno |
| 3,255,924 | A | 6/1966 | Modderno |
| 3,608,782 | A | 9/1971 | Sahicq |
| 4,021,338 | A | 5/1977 | Harkin |
| 4,130,198 | A | 12/1978 | Aho |
| 4,264,007 | A | 4/1981 | Hunt |
| 4,297,298 | A | 10/1981 | Crommelynch et al. |
| 4,311,598 | A | 1/1982 | Verachtert |
| 4,315,570 | A | 2/1982 | Silver et al. |
| 4,321,255 | A | 3/1982 | Boden |
| 4,371,094 | A | 2/1983 | Hutter, III |
| 4,414,127 | A | 11/1983 | Fu |
| 4,509,641 | A | 4/1985 | Scieri et al. |
| 4,618,444 | A | 10/1986 | Hudson et al. |
| 4,651,899 | A | 3/1987 | Pauls et al. |
| 4,655,975 | A | 4/1987 | Snoble |
| 4,750,615 | A | 6/1988 | Kaufeler |
| 4,779,763 | A | 10/1988 | Klawitter |
| 4,808,006 | A | 2/1989 | Kaufeler |
| 4,826,658 | A | 5/1989 | Kay |
| 4,832,968 | A | 5/1989 | Forage et al. |
| 4,915,955 | A | 4/1990 | Gomori |
| 5,152,965 | A | 10/1992 | Fisk et al. |
| 5,186,323 | A | 2/1993 | Pleger |
| 5,291,991 | A | 3/1994 | Meyer |
| 5,349,083 | A | 9/1994 | Brougham et al. |
| 5,357,636 | A | 10/1994 | Dresdner et al. |
| 5,368,867 | A | 11/1994 | Da Silva et al. |
| 5,405,051 | A | 4/1995 | Miskell |
| 5,409,141 | A | 4/1995 | Kikuchi et al. |
| 5,419,445 | A | 5/1995 | Kaesemeyer |

(Continued)

FOREIGN PATENT DOCUMENTS

| GB | 2189394 | 10/1987 |
|---|---|---|
| WO | WO 03/080231 | 10/2003 |

(Continued)

OTHER PUBLICATIONS

Klenk et al. Peroxy Compounds, Organic. Ullmann's Encyclopedia of Industrial Chemistry. Published Online: Jun. 15, 2000; DOI: 10.1002/14356007.a19_199).*
Brady et al.; Persistent silver disinfectant for the environmental control of pathogenic bacteria; American Journal of Infection Control; Jun. 2003; pp. 208-214; vol. 31, Issue 4; The Association for Professionals in Infection Control and Epidemiology, Inc.
Brentano; et al.; Antibacterial efficacy of a colloidal silver complex; Surgical Forum; 1966; pp. 76-78; vol. 17; Journal of the American College of Surgeons.
Monarca et al.; Decontamination of dental unit waterlines using disinfectants and filters (Abstract only); Minerva Stomatologica; Oct. 2002; vol. 10; Italian Society of Odontsotomatology and Maxillio-Facial Surgery.
Pedahzur et al.; The interaction of silver ions and hydrogen peroxide in the inactivation of e. coli: a preliminary evaluation of a new long lasting residual drinking water disinfectant; Water Science and Technology; 1995; pp. 123-129; vol. 31, No. 5-6; Pergamon.

(Continued)

Primary Examiner — Bethany Barham
Assistant Examiner — Peter Anthopolos
(74) Attorney, Agent, or Firm — Thorpe North & Western LLP

(57) ABSTRACT

The present disclosure is drawn to a disinfectant system which can be used to disinfect surfaces. The system includes a first chamber containing a first solution and a second chamber containing a second solution. The first solution can include an alcohol, an organic carboxylic acid, and from 0.01 ppm, to 1,000 ppm by weight of a transition metal or alloy thereof based on the first solution weight content. The second solution can include hydrogen peroxide. The system further includes a dispenser through which the system is configured to mix and dispense the first solution and the second solution immediately before being dispensed. A peracid composition is formed upon mixing of the first and second solutions.

18 Claims, No Drawings

(56) References Cited

U.S. PATENT DOCUMENTS

| | | | |
|---|---|---|---|
| 5,419,908 A | 5/1995 | Richter et al. | |
| 5,437,858 A | 8/1995 | Hungerbach et al. | |
| 5,494,644 A | 2/1996 | Thomas et al. | |
| 5,508,046 A | 4/1996 | Cosentino et al. | |
| 5,563,132 A | 10/1996 | Bodaness | |
| 5,638,992 A | 6/1997 | Lim et al. | |
| 5,709,870 A | 1/1998 | Yoshimura et al. | |
| 5,730,326 A | 3/1998 | Kaeser | |
| 5,772,017 A | 6/1998 | Kang | |
| 5,813,557 A | 9/1998 | Oratz | |
| 5,824,267 A | 10/1998 | Kawasumi et al. | |
| 5,875,889 A | 3/1999 | Albisetti | |
| 5,945,032 A | 8/1999 | Breitenbach et al. | |
| 5,951,993 A | 9/1999 | Scholz et al. | |
| 5,977,403 A | 11/1999 | Byers | |
| 5,997,585 A | 12/1999 | Scialla et al. | |
| 6,021,892 A | 2/2000 | Baudin | |
| 6,027,469 A | 2/2000 | Johnson | |
| 6,073,803 A | 6/2000 | Sturm et al. | |
| 6,085,945 A | 7/2000 | Fransen | |
| 6,114,298 A | 9/2000 | Petri et al. | |
| 6,152,296 A | 11/2000 | Shih | |
| 6,189,735 B1 | 2/2001 | Plasmati-Luchinger | |
| 6,197,814 B1 | 3/2001 | Arata | |
| 6,200,946 B1 | 3/2001 | Blume et al. | |
| 6,218,351 B1 | 4/2001 | Busch et al. | |
| 6,231,848 B1 | 5/2001 | Breitenbach et al. | |
| 6,242,009 B1 | 6/2001 | Batarseh et al. | |
| 6,257,253 B1 | 7/2001 | Lentsch et al. | |
| 6,277,414 B1* | 8/2001 | Elhaik et al. | 424/616 |
| 6,293,433 B1 | 9/2001 | Joulia | |
| 6,302,968 B1 | 10/2001 | Baum et al. | |
| 6,368,611 B1 | 4/2002 | Whitbourne et al. | |
| 6,379,712 B1 | 4/2002 | Yan et al. | |
| 6,401,975 B2 | 6/2002 | Diaz et al. | |
| 6,436,342 B1 | 8/2002 | Petri et al. | |
| 6,524,624 B1 | 2/2003 | Morelli et al. | |
| 6,540,791 B1 | 4/2003 | Dias | |
| 6,543,612 B2 | 4/2003 | Lee et al. | |
| 6,569,353 B1 | 5/2003 | Giletto et al. | |
| 6,583,176 B2 | 6/2003 | Arata et al. | |
| 6,630,172 B2 | 10/2003 | Batarseh | |
| 6,660,289 B1* | 12/2003 | Wilmotte et al. | 424/405 |
| 6,743,348 B2 | 6/2004 | Holladay et al. | |
| 6,797,302 B1 | 9/2004 | Ben Yehuda et al. | |
| 6,827,766 B2 | 12/2004 | Carnes et al. | |
| 6,851,580 B2 | 2/2005 | Stank et al. | |
| 6,866,145 B2 | 3/2005 | Richards et al. | |
| 6,939,564 B2 | 9/2005 | Ranger et al. | |
| 6,939,566 B2 | 9/2005 | Batarseh et al. | |
| 6,959,807 B2 | 11/2005 | Sharon et al. | |
| 6,962,714 B2 | 11/2005 | Hei et al. | |
| 7,033,511 B2 | 4/2006 | Zawada et al. | |
| 7,083,043 B2 | 8/2006 | Sharon | |
| 7,124,788 B2 | 10/2006 | Pericard | |
| 7,131,784 B2 | 11/2006 | Lee et al. | |
| 7,287,670 B2 | 10/2007 | Yoshida et al. | |
| 7,351,684 B2 | 4/2008 | Tichy et al. | |
| 7,377,383 B2 | 5/2008 | Henry | |
| 7,462,590 B2 | 12/2008 | Tichy et al. | |
| 7,473,675 B2 | 1/2009 | Tichy et al. | |
| 7,504,369 B2 | 3/2009 | Tichy et al. | |
| 7,507,701 B2 | 3/2009 | Tichy et al. | |
| 7,511,007 B2 | 3/2009 | Tichy et al. | |
| 7,534,756 B2 | 5/2009 | Tichy et al. | |
| 7,553,805 B2 | 6/2009 | Tichy et al. | |
| 8,464,910 B2 | 6/2013 | Larson | |
| 8,716,339 B2 | 5/2014 | Larson et al. | |
| 8,789,716 B2 | 7/2014 | Larson et al. | |
| 2002/0108968 A1 | 8/2002 | Dumont | |
| 2002/0137648 A1 | 9/2002 | Sharma et al. | |
| 2003/0008797 A1 | 1/2003 | Hage et al. | |
| 2003/0099717 A1 | 5/2003 | Cabrera | |
| 2003/0235623 A1 | 12/2003 | Van Oosterom | |
| 2004/0067159 A1 | 4/2004 | Carnes et al. | |
| 2004/0089372 A1 | 5/2004 | Higgins et al. | |
| 2004/0170742 A1 | 9/2004 | Ben Yehuda et al. | |
| 2004/0234569 A1 | 11/2004 | Nakada et al. | |
| 2005/0013836 A1 | 1/2005 | Raad | |
| 2005/0194357 A1 | 9/2005 | Liu et al. | |
| 2005/0256017 A1 | 11/2005 | Dykstra | |
| 2005/0256200 A1 | 11/2005 | Burkhart et al. | |
| 2006/0035808 A1 | 2/2006 | Ahmed et al. | |
| 2006/0122082 A1 | 6/2006 | Paul | |
| 2006/0182813 A1 | 8/2006 | Holladay | |
| 2006/0198798 A1 | 9/2006 | Tichy et al. | |
| 2006/0199752 A1* | 9/2006 | Tichy et al. | 510/375 |
| 2006/0240381 A1 | 10/2006 | Rizolu et al. | |
| 2006/0263239 A1 | 11/2006 | Tichy et al. | |
| 2006/0289316 A1 | 12/2006 | Henry | |
| 2007/0003603 A1* | 1/2007 | Karandikar et al. | 424/443 |
| 2007/0048175 A1 | 3/2007 | Tichy et al. | |
| 2007/0059202 A1* | 3/2007 | Tichy et al. | 422/28 |
| 2007/0073081 A1 | 3/2007 | Fisher | |
| 2007/0167340 A1 | 7/2007 | Barthel et al. | |
| 2007/0215496 A1 | 9/2007 | Scarborough | |
| 2007/0254044 A1 | 11/2007 | Karandikar et al. | |
| 2008/0000931 A1* | 1/2008 | Tichy et al. | 222/212 |
| 2008/0083779 A1 | 4/2008 | Saravanane et al. | |
| 2009/0004289 A1 | 1/2009 | Tichy | |
| 2009/0053323 A1 | 2/2009 | Tichy | |
| 2009/0232860 A1 | 9/2009 | Larson | |
| 2010/0074967 A1 | 3/2010 | Tichy | |
| 2010/0116346 A1 | 5/2010 | Larson | |
| 2010/0120913 A1 | 5/2010 | Larson | |
| 2010/0143496 A1 | 6/2010 | Larson | |

FOREIGN PATENT DOCUMENTS

| | | |
|---|---|---|
| WO | WO 2005/000324 | 1/2005 |
| WO | WO 2006/079109 | 7/2006 |
| WO | WO 2006/093792 | 9/2006 |
| WO | WO 2009/114754 | 9/2009 |
| WO | WO 2010/056871 | 5/2010 |
| WO | WO 2010/056881 | 5/2010 |

OTHER PUBLICATIONS

Phillips; et al.; Chemical Disinfectant; Annual Review of Microbiology; Oct. 1958; pp. 525-550; vol. 12; Annual Reviews.
Psi; Container Venting; http://www.psix.com/containerventing.html; accessed online Nov. 12, 2008; 1 page; Performance Systematix, Inc.
Psi; Container Venting. Circumvent & Air Foil; http://www.psix.com/ev_products_circumvent.html; Accessed online Nov. 12, 2008; 2 pages; Performance Systematix, Inc.
Psi; Container Venting Linerless Applications; http://www.psix.conit/cv_products_linerless.html; Accessed online Nov. 12, 2008; 1 page; Performance Systematix, Inc.
Psi; Container Venting. Problems We Solve; http://www.psix.corn/cv_problems.html; accessed online Nov. 12, 2008; 2 pages; Performance Systematix, Inc.
Psi; Venting Products, Curcumvent & Air Foil; psi brochure; Oct. 2006; 4 pages; Performance Systems Inc.
Seaquist Perfect Dispensing; Bag On Valve; http://seaquistperfect,com/PAGES/EP/BOV.html; Accessed online Mar. 3, 2008; 2 pages; Seaquist Perfect Dispensing.
Seaquist Perfect Dispensing; Fusion; http://www.seaquistperfect.com/PAGES/CO_DISPENSING/fusion.html; Accessed online Mar. 3, 2008; 2 pages; Seaquist Perfect Dispensing.
Schuster et al; Persistent silver disinfectant for the environmental myth and reality; American Journal of Infection Control; Jun. 2003; pp. 309-311; vol. 32; The Association for Professionals inInfection Control and Epidemiology, Inc.
Surdeau et al.; Sensitivity of bacterial biofilms and planktonic cells to a new antimicrobial agent, Oxsil 320N; Journal of Hospital Infection; 2006; pp. 487-493; vol. 62; Elsevier.
Virosil F&B; Swift Virucidal with Swiss Precision; http://web.archive.org/web/20060217191603/http://sanosilbiotech.com/start_food.html; Accessed online Nov, 9, 2007; 5 pages; Sanosil.
Yin et al.; Analysis of Diacyl Peroxides by Ag+ Coordination Ionspray Tandem Mass Spectrometry: Free Radical Pathways of Complex Decomposition; Journal of the American Society of Mass Spectrometry; Apr. 2001; pp. 449-455; vol. 12; American Society for Mass Spectrometry/Elsevier.

* cited by examiner

TWO-PART DISINFECTANT SYSTEM AND RELATED METHODS

This application is a continuation of U.S. patent application Ser. No. 12/617,521 filed on Nov. 12, 2009, which claims the benefit of U.S. Provisional Application Ser. No. 61/113,946 filed on Nov. 12, 2008, each of which are incorporated herein by reference in their entirety.

FIELD OF THE INVENTION

The present disclosure is drawn to disinfectant systems that can be used for a variety of purposes, including for hard surface cleaning, and which are effective as disinfectants or even sterilants.

BACKGROUND OF THE INVENTION

Disinfectants and sterilants, such as hard surface disinfectants and sterilants, are widely used in both domestic and professional settings. Exemplary of a commonly used hard surface cleaner is Lysol® disinfectant. Though Lysol® is effective for many applications, Lysol® is not as effective at reducing levels of bacteria as commercially available glutaraldehyde aqueous solutions. Glutaraldehyde aqueous solutions are widely used as disinfectants (and often as sterilants), and are commonly available in 1 wt % and 2 wt % solutions, particularly in medical and dental settings. Glutaraldehyde solutions are typically used for more delicate medical/dental instruments that would otherwise be susceptible to damage by other sterilization methods, e.g., autoclaving. However, glutaraldehyde is also a powerful irritant and respiratory sensitizer. In fact, there have been reports of sensitization of individuals due to the fumes, which have lead to respiratory problems, headaches, lethargy, discoloring of the skin, etc. Because of these issues related to glutaraldehyde fumes, air quality must often be monitored, or appropriate air ventilation must be present. As a result, though glutaraldehyde solutions are relatively effective disinfectants, and even sterilants, it would be desirable to provide disinfectant systems that can exhibit effective bacteria kill levels, and at the same time be safer for the individuals using the disinfectant/sterilant.

SUMMARY OF THE INVENTION

It has been recognized that it would be desirable to provide a disinfectant system that can effectively clean and disinfect surfaces, particularly hard surfaces. In accordance with this, a disinfectant system is provided which includes a first chamber containing a first solution and a second chamber containing a second solution. The first solution can include an alcohol, an organic carboxylic acid, and from 0.01 ppm, to 1,000 ppm by weight of a transition metal or alloy thereof based on the first solution weight content. The second solution can include an activator. The system is configured for mixing the first solution with the second solution immediately before use and further includes a dispenser through which the system is configured to dispense a mixture of the first solution and the second solution. When the first solution and second solution are mixed a peracid is formed.

Additional features and advantages of the invention will be apparent from the detailed description that follows, which illustrates, by way of example, features of the invention.

DETAILED DESCRIPTION OF THE PREFERRED EMBODIMENT(S)

Reference will now be made to the exemplary embodiments, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention. It is also to be understood that the terminology used herein is used for the purpose of describing particular embodiments only. The terms are not intended to be limiting unless specified as such.

It must be noted that, as used in this specification and the appended claims, the singular forms "a," "an," and "the" include plural referents unless the content clearly dictates otherwise.

The term "solution" is also used throughout the specification to describe the liquid components of the disinfectant systems of the present disclosure. However, as these "solutions" include colloidal transition metals, these components can also be described as dispersions or suspensions. As the continuous phase is typically a solution, and the transition metal is present as a colloid, for convenience, these components will typically be referred to as "solutions" herein.

The term "food grade" when used with respect to ingredients or components used in the systems of the present disclosure refers to ingredients or components that are substantially free from ingredients which would be considered harmful or toxic to a mammal upon consumption above levels that are generally recognized as safe.

The term "substantially free" when used with regard to the disinfectant systems of the present disclosure refers to the total absence of or near total absence of a specific compound or composition. For example, when a disinfectant system is said to be substantially free of aldehydes, there are either no aldehydes in the disinfectant system or only trace amounts of aldehydes in the system.

The term "colloidal transition metals" refers to colloidal particles of elemental transitional metals or the alloys of such elemental transition metals. Colloidal transition metals are distinct from salts and oxides of transition metals. Accordingly, compounds such as silver oxide, silver nitrate, silver chloride, silver bromide, silver iodide, and the like are not colloidal transition metals under the present invention.

The term "activator" refers to compounds that, when allowed to contact an organic carboxylic acid, can provide for the generation of a peracid compound. It is noteworthy that the peracid compound formed may have a short life-span due to the natural degradation of peracid compounds. Non-limiting examples of activators that can be used include methyl ethyl ketone peroxide, ozone, hydrogen peroxide, carbamide (urea) peroxide, metal peroxides such as potassium superoxide, lithium peroxide, barium peroxide, sodium peroxide, calcium peroxide, strontium peroxide, magnesium peroxide, sodium percarbonate peroxide, sodium peroxide, potassium peroxide, other peroxide compounds, combinations thereof, and the like.

In describing embodiments of the disinfectant systems of the present disclosure, reference will be made to "first" or "second" as they relate to chambers, or solutions, etc. It is noted that these are merely relative terms, and a chamber or solution described or shown as a "first" chamber or solution could just as easily be referred to a "second" chamber or solution, and such description is implicitly included herein.

Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight ratio range of about 1 wt % to about 20 wt % should be interpreted to include not only the explicitly recited limits of 1 wt % and about 20 wt %, but also to include individual weights such as 2 wt %, 11 wt %, 14 wt %, and sub-ranges such as 10 wt % to 20 wt %, 5 wt % to 15 wt %, etc.

In accordance with this, a disinfectant system is provided which includes a first chamber containing a first solution and a second chamber containing a second solution. The first solution can include an alcohol, an organic carboxylic acid, and from 0.01 ppm, to 1,000 ppm by weight of a transition metal or alloy thereof based on the first solution weight content. The second solution can include an activator. The system further includes a dispenser through which the system is configured to dispense the first solution and the second solution, the solutions being mixed immediately before their use or application. Once the first solution and second solution are mixed, a peracid can be formed.

The disinfectant system of the present disclosure can take on any two-chambered configuration so long as the contents of the two chambers, namely the first solution and the second solution, remain separate and apart until the disinfectant is needed. In one embodiment, the system first and second chamber can both be pressurized. The pressurization of the chambers can allow for the solutions present in the chambers to be expelled rapidly and mixed as they are dispensed. The mixing can occur as a function of the two liquids coming together in the dispenser or the mixing can occur in a mixing chamber placed in the system through which both solutions would pass on their way to the dispenser. The system of the present disclosure can use any mixing mechanism known in the art so long as the mixing occurs immediately before application of the disinfectant.

As shown in the examples, the disinfectant system of the present disclosure can be used effectively against a wide array of bacteria. Without being limited by theory, it is believed that the extraordinary effectiveness of the system as a disinfectant is due, at least in part, to the momentary formation of peracids when the first solution and second solution of the system are mixed and dispensed through the system dispenser. For example, in a system that utilizes acetic acid, the addition of an activator, such as hydrogen peroxide or others described herein, from the second solution can result in a reaction in which peracetic acid and water are produced in equilibrium as follows:

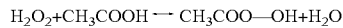

Once formed and dispensed on the surface, it is believed that the peracids aid in disinfecting the surface in a rapid and effective manner before they break down or are used up. By waiting to combine the two solutions of the disinfectant system of the present disclosure until just before application, the peracids are just formed or are forming as the mixed solutions contact the target surface. It is believed that if the solutions were combined significantly before application to the surface, the peracids would not be present, or at least not in significant enough concentrations, and that the effectiveness of the solutions would not be equivalent to that of the present system.

As disclosed above, the first solution present in the first chamber of the system can include an alcohol, transition metal, and an organic carboxylic acid. The alcohol present in the first solution can be a single alcohol or a combination of multiple alcohols. One example of alcohols which can be used in the first solution are aliphatic alcohols and other carbon-containing alcohols, having from 1 to 24 carbons ($C_1$-$C_{24}$ alcohol), It is to be noted that "$C_1$-$C_{24}$ alcohol" does not necessarily imply only straight chain saturated aliphatic alcohols, as other carbon-containing alcohols can also be used within this definition, including branched aliphatic alcohols, alicyclic alcohols, aromatic alcohols, unsaturated alcohols, as well as substituted aliphatic, alicyclic, aromatic, and unsaturated alcohols, etc. In one embodiment, the aliphatic alcohols can be $C_1$ to $C_5$ alcohols including methanol, ethanol, propanol and isopropanol, butanols, and pentanols, due to their availability and lower boiling points. Polyhydric alcohols can also be used alone or in combination with other alcohols. Non-limiting examples of polyhydric alcohols which can be used in the present disclosure include but are not limited to ethylene glycol (ethane-1,2-diol)glycerin (or glycerol, propane-1,2,3-triol), propane-1,2-diol, polyvinyl alcohol, sorbitol, other polyols, and the like. Other non-aliphatic alcohols may also be used including but not limited to phenols and substituted phenols, erucyl alcohol, ricinolyl alcohol, arachidyl alcohol, capryl alcohol, capric alcohol, behenyl alcohol, lauryl alcohol (1-dodecanol), myristyl alcohol (1-tetradecanol), cetyl (or palmityl) alcohol (1-hexadecanol), stearyl alcohol (1-octadecanol), isostearyl alcohol, oleyl alcohol (cis-9-octadecen-1-ol), palmitoleyl alcohol, linoleyl alcohol (9Z,12Z-octadecadien-1-ol), elaidyl alcohol (9E-octadecen-1-ol), elaidolinoleyl alcohol (9E,12E-octadecadien-1-ol), linolenyl alcohol (9Z,12Z,15Z-octadecatrien-1-ol), elaidolinolenyl alcohol (9E,12E,15-E-octadecatrien-1-ol), combinations thereof and the like.

In some embodiments, for practical considerations, methanol, ethanol, and denatured alcohols (mixtures of ethanol and smaller amounts of methanol, and optionally, minute amounts of benzene, ketones, acetates, etc.) can often be preferred for use because of their availability and cost. If the desire is to provide a food grade or food safe system, then alcohols can be selected that satisfy this requirement. The concentrations of the alcohol in the first solution of the system can be from about 0.05 wt % to about 10 wt %. In one embodiment the concentration of the alcohol in the first solution is about 0.1 wt % to about 5 wt %. In another embodiment, the concentration of the alcohol in the first solution is about 0.1 wt % to about 1 wt %.

Regarding the transition metal, in accordance with the embodiments of the present disclosure, the metal can be in ionic form (e.g. a metal salt) and/or colloidal form, i.e. elemental colloids or colloids of metal alloys. In one specific embodiment, the transition metal can be in a sub-micron form (i.e. dispersion of less than 1 μm metal colloidal particles). However, larger colloidal transition metal particles can also be used in certain applications. Typical transition metals that are desirable for use include Group VI to Group XI transition metals, and more preferably, can include Group X to Group XI transition metals. Alloys including at least one metal from the Group VI to Group XI metals can also be used. Further, when colloidal metals are dispersed in a colloidal solution, there is often an amount of the metal in ionic or salt form that is also present in the suspension solution. For example, colloidal silver may include a certain percentage of a silver salt or ionic silver in solution, e.g., 10% to 90% by weight of metal content can be ionic based on the total metal content.

This being stated, certain preferred metals for use in accordance with embodiments of the present disclosure are ruthenium, rhodium, osmium, iridium, palladium, platinum, copper, gold, silver, alloys thereof, and mixtures thereof. Silver is often the most preferred, depending on the application, the levels of kill that are desired or required, the type of pathogen being targeted, the substrate that is being cleaned, etc. Any of these embodiments can also benefit from the use of alloys. For Example, certain combinations of metals in an alloy may provide an acceptable kill level for a specific pathogen, and also provide benefits that are related more to secondary consideration, such as solution stability, substrate to be cleaned, etc. Preferred examples of transition metal alloys for use in the present disclosure include but are not limited to copper-silver allows, silver-manganese alloys, iron-copper alloys, chromium-silver alloys, gold-silver alloys, and magnesium-silver alloys.

The transition metal or alloy thereof can be present in the first solution at a concentration of about 0.01 ppm, to about 1,000 ppm. In one embodiment, the transition metal or alloy thereof can be present in the first solution at about 1 ppm to about 500 ppm. In yet another embodiment, the transition metal or alloy thereof can be present in the first solution at about 10 ppm to 350 ppm by weight.

The organic acid present in the first solution of the disinfectant system can generally be any organic acid which can effectively form a peracid which is effective as a disinfecting agent. Non-limiting examples of acids which can be used include formic acid, acetic acid, oxalic acid, propanoic acid, lactic acid, butanoic acid, pentanoic acid, hexanoic acid, adipic acid, citric, benzoic acid, and mixtures thereof. In one embodiment, the organic carboxylic acid is citric acid. In another embodiment, the organic carboxylic acid is acetic acid. The organic carboxylic acid can be present in the first solution at about 3 wt % to about 20 wt %. In one embodiment, the organic carboxylic acid can be present in the first solution at about 5 wt % to about 15 wt %. In yet another embodiment, the organic carboxylic acid can be present in the first solution at about 7 wt % to about 13 wt %.

The first solution of the disinfectant system of the present disclosure can have any type of liquid carrier system known in the art. Generally, the liquid carrier will be largely aqueous, although water need not comprise the majority of the carrier.

The second solution of the disinfectant system of the present disclosure can include an aqueous solution of and an activator, such as hydrogen peroxide, a metal peroxide, ozone, etc. The activator may be present in the second solution at from about 0.01 wt % to about 10 wt %. In another embodiment, the activator can be present in the second solution at from about 0.1 to about 9 wt %. In yet another embodiment, the activator is present in the second solution at from about 0.5 wt % to about 7 wt %.

In one embodiment of the system of the present disclosure, the disinfectant system can be substantially free of non-food-grade or food safe ingredients. For example, though not required, the disinfectant system can be substantially free of ingredients commonly present in many commercially available surface cleaners. Examples of non-food-grade ingredients which can be omitted from the disinfectants or sterilants of the present disclosure include, but are not limited to, aldehydes such as glutaraldehyde; chlorine and bromine-containing components, iodophore-containing components, phenolic-containing components, quaternary ammonium-containing disinfectants; and the like.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Preparation of Disinfectant System

An aqueous disinfectant system is prepared in accordance with embodiments of the present disclosure, which includes the following ingredients in approximate amounts:
First solution:
10 wt % citric acid
0.05% polyvinyl alcohol
Balance 150 ppm silver colloids in water
Second solution:
5 wt % hydrogen peroxide in water
The first solution and the second solution were each placed in separate chambers from which they could be withdrawn and mixed through a dispenser.

Example 2

Preparation of Disinfectant System

An aqueous disinfectant system is prepared in accordance with embodiments of the present disclosure, which includes the following ingredients in approximate amounts:
First solution:
10 wt % citric acid
0.05% polyvinyl alcohol
Balance 300 ppm silver colloid in water
Second solution:
5 wt % hydrogen peroxide in water
The first solution and the second solution were each placed in separate chambers from which they could be withdrawn and mixed through a dispenser.

Example 3

Kill-Time Studies of *Staphylococcus aureus* Using Disinfectants of Examples 1 and 2

A study was conducted to determine the antimicrobial activity of the disinfectant systems of Example 1 and Example 2 when challenged with an organic load, on the test organism *Staphylococcus aureus*. This was accomplished by performing a standard AOAC Germicidal Spray Product as Disinfectants Protocol; Method 961.02 using test organisms dried onto glass slides which were sprayed 3 seconds and held for 1, 5, and 10 minutes prior to subculture.

Specifically, the test suspension was prepared by growing a culture of *Staphylococcus aureus*, ATCC 6538, in Nutrient Broth at 37° C., for 48 hour. A 10 µaliquot of the test culture was transferred to 1"×1" square glass slides in Petri dishes using a calibrated micropipette. The inoculum was immediately spread evenly over the entire surface of the slide. The dish was covered, and the process was repeated until 10 slides per time point were inoculated.

The slides were then dried in a 37° C. incubator for 30-40 minutes. The slides with *S. aureus*, 10 per Example 1 and Example 2 per time period (60 total), were sprayed with the test disinfectant using the system of Examples 1 and 2. The slides were sprayed for 3 seconds at a distance of about 6-8 inches from the slides. The slides were held for 1, 5, and 10 minutes, and then excess liquid was drained from the slides. The slides were then transferred to individual 32×200 mm glass culture tubes containing 20 ml Fluid Thioglycollate broth and shaken thoroughly. All of the tubes were incubated at 37° C. for 48 hours. The tubes were then observed for growth (+) or no growth (−) by visual turbidity.

As a control two inoculated, but unsprayed slides prepared as described above were used. A media control containing no slide was also included. To check for bacteriostasis, a few representative negative subculture tubes are evaluated for residual disinfectant bacteriostasis by inoculating each with a small look contaminated with a respective test culture suspension and re-incubating the tubes at 37° C. for 24 hours.

The results of the test are provided as follows:

TABLE 1

Test Results after 1 minute contact time

| Tube number | Example 1 Growth (+ or −) | Example 2 Growth (+ or −) |
|---|---|---|
| 1 | − | − |
| 2 | − | − |
| 3 | − | − |
| 4 | − | − |
| 5 | − | − |
| 6 | − | − |
| 7 | − | − |
| 8 | − | − |
| 9 | − | − |
| 10 | − | − |

TABLE 2

Test Results after 5 minute contact time

| Tube number | Example 1 Growth (+ or −) | Example 2 Growth (+ or −) |
|---|---|---|
| 1 | − | − |
| 2 | − | − |
| 3 | − | − |
| 4 | − | − |
| 5 | − | − |
| 6 | − | − |
| 7 | − | − |
| 8 | − | − |
| 9 | − | − |
| 10 | − | − |

TABLE 3

Test Results after 10 minute contact time

| Tube number | Example 1 Growth (+ or −) | Example 2 Growth (+ or −) |
|---|---|---|
| 1 | − | − |
| 2 | − | − |
| 3 | − | − |
| 4 | − | − |
| 5 | − | − |
| 6 | − | − |
| 7 | − | − |
| 8 | − | − |
| 9 | − | − |
| 10 | − | − |

TABLE 4 control

| Sample | Growth (= or −) |
|---|---|
| S. Aureus positive control 1 | + |
| S. Aureus positive control 2 | + |
| Media Control | − |

TABLE 5

Bacteriostasis controls

| Tube | Growth (+ or −) |
|---|---|
| Spray 1, 1-min Tube 1 | + |
| Spray 1, 1-min, Tube 2 | + |
| Spray 1, 5-min Tube 1 | + |
| Spray 1, 5-min Tube 2 | + |
| Spray 1, 10-min Tube 1 | + |
| Spray 1, 10-min Tube 2 | + |
| Spray 2, 1-min Tube 1 | + |
| Spray 2, 1-min Tube 2 | + |
| Spray 2, 5-min Tube 1 | + |
| Spray 2, 5-min Tube 2 | + |
| Spray 2, 10-min Tube 1 | + |
| Spray 2, 10-min Tube 2 | + |

All controls produced the expected results. The positive control slides that were not treated with disinfectant showed characteristic growth for *S. aureus*. The media control tube with no slide showed no growth. The re-inoculated bacteriostasis control tubes all showed positive growth upon re-incubation, indicating no bacteriostasis from the residual disinfectant left on the slides.

The two-part systems of Example 1 and 2 were able to completely kill the dried organisms on all of the slides for all of the time points. Since killing of ten out of ten slides is a required to pass the AOAC Germicidal Spray test, the systems passed the test at the 1, 5, and 10 minutes contact times.

Example 4

Kill-Time Studies of *Salmonella choleraesuis* Using Disinfectants of Examples 1 and 2

A study was conducted to determine the antimicrobial activity of the disinfectant systems of Example 1 and Example 2 when challenged with an organic load, on the test organism *Salmonella choleraesuis*. This was accomplished by performing a standard AOAC Germicidal Spray Product as Disinfectants Protocol; Method 961.02 using test organisms dried onto glass slides which were sprayed 3 seconds and held for 1, 5, and 10 minutes prior to subculture.

Specifically, the test suspension was prepared by growing a culture of *Salmonella choleraesuis*, ATCC 10708, in Nutrient Broth at 37° C., for 48 hour. A 10 µaliquot of the test culture was transferred to 1"×1" square glass slides in Petri dishes using a calibrated micropipette. The inoculum was immediately spread evenly over the entire surface of the slide. The dish was covered, and the process was repeated until 10 slides per time point were inoculated.

The slides were then dried in a 37° C. incubator for 30-40 minutes. The slides with *Salmonella choleraesuis*, 10 per Example 1 and Example 2 per time period (60 total), were sprayed with the test disinfectant using the system of Examples 1 and 2. The slides were sprayed for 3 seconds at a distance of about 6-8 inches from the slides. The slides were held for 1, 5, and 10 minutes, and then excess liquid was drained from the slides. The slides were then transferred to individual 32×200 mm glass culture tubes containing 20 ml Fluid Thioglycollate broth and shaken thoroughly. All of the tubes were incubated at 37° C. for 48 hours. The tubes were then observed for growth (+) or no growth (−) by visual turbidity.

As a control two inoculated, but unsprayed slides prepared as described above were used. A media control containing no slide was also included. To check for bacteriostasis, a few representative negative subculture tubes are evaluated for residual disinfectant bacteriostasis by inoculating each with a small look contaminated with a respective test culture suspension and re-incubating the tubes at 37° C. for 24 hours.

The results of the test are provided as follows:

TABLE 6

Test Results after 1 minute contact time

| Tube number | Example 1 Growth (+ or −) | Example 2 Growth (+ or −) |
|---|---|---|
| 1 | − | − |
| 2 | − | − |
| 3 | − | − |
| 4 | − | − |
| 5 | − | − |
| 6 | − | − |
| 7 | − | − |
| 8 | − | − |
| 9 | − | − |
| 10 | − | − |

TABLE 7

Test Results after 5 minute contact time

| Tube number | Example 1 Growth (+ or −) | Example 2 Growth (+ or −) |
|---|---|---|
| 1 | − | − |
| 2 | − | − |
| 3 | − | − |
| 4 | − | − |
| 5 | − | − |
| 6 | − | − |
| 7 | − | − |
| 8 | − | − |
| 9 | − | − |
| 10 | − | − |

TABLE 8

Test Results after 10 minute contact time

| Tube number | Example 1 Growth (+ or −) | Example 2 Growth (+ or −) |
|---|---|---|
| 1 | − | − |
| 2 | − | − |
| 3 | − | − |
| 4 | − | − |
| 5 | − | − |
| 6 | − | − |
| 7 | − | − |
| 8 | − | − |
| 9 | − | − |
| 10 | − | − |

TABLE 9 control

| Sample | Growth (= or −) |
|---|---|
| *Salmonella choleraesuis* positive control 1 | + |
| *Salmonella choleraesuis* positive control 2 | + |
| Media Control 1 | − |
| Media Control 2 | − |

TABLE 10

Bacteriostasis controls

| Tube | Growth (+ or −) |
|---|---|
| Spray 1, 1-min Tube 1 | + |
| Spray 1, 5-min Tube 1 | + |
| Spray 1, 10-min Tube 1 | + |
| Spray 2, 1-min Tube 1 | + |
| Spray 2, 5-min Tube 1 | + |
| Spray 2, 10-min Tube 1 | + |

All controls produced the expected results. The positive control slides that were not treated with disinfectant showed characteristic growth for *Salmonella choleraesuis*. The media control tube with no slide showed no growth. The re-inoculated bacteriostasis control tubes all showed positive growth upon re-incubation, indicating no bacteriostasis from the residual disinfectant left on the slides.

The two-part systems of Example 1 and 2 were able to completely kill the dried organisms on all of the slides for all of the time points. Since killing of ten out of ten slides is a required to pass the AOAC Germicidal Spray test, the systems passed the test at the 1, 5, and 10 minutes contact times.

Example 5

Kill-Time Studies of *Pseudomonas aeruginosa* Using Disinfectants of Examples 1 and 2

A study was conducted to determine the antimicrobial activity of the disinfectant systems of Example 1 and Example 2 when challenged with an organic load, on the test organism *Pseudomonas aeruginosa*. This was accomplished by performing a standard AOAC Germicidal Spray Product as Disinfectants Protocol; Method 961.02 using test organisms dried onto glass slides which were sprayed 3 seconds and held for 1, 5, and 10 minutes prior to subculture.

Specifically, the test suspension was prepared by growing a culture of *Pseudomonas aeruginosa*, ATCC 10708, in Nutrient Broth at 37° C., for 48 hour. A 10 μaliquot of the test culture was transferred to 1"×1" square glass slides in Petri dishes using a calibrated micropipette. The inoculum was immediately spread evenly over the entire surface of the slide. The dish was covered, and the process was repeated until 10 slides per time point were inoculated.

The slides were then dried in a 37° C. incubator for 30-40 minutes. The slides with *Pseudomonas aeruginosa*, 10 per Example 1 and Example 2 per time period (60 total), were sprayed with the test disinfectant using the system of Examples 1 and 2. The slides were sprayed for 3 seconds at a distance of about 6-8 inches from the slides. The slides were held for 1, 5, and 10 minutes, and then excess liquid was drained from the slides. The slides were then transferred to individual 32×200 mm glass culture tubes containing 20 ml Fluid Thioglycollate broth and shaken thoroughly. All of the tubes were incubated at 37° C. for 48 hours. The tubes were then observed for growth (+) or no growth (−) by visual turbidity.

As a control two inoculated, but unsprayed slides prepared as described above were used. A media control containing no slide was also included. To check for bacteriostasis, a few representative negative subculture tubes are evaluated for residual disinfectant bacteriostasis by inoculating each with a small look contaminated with a respective test culture suspension and re-incubating the tubes at 37° C. for 24 hours.

The results of the test are provided as follows:

TABLE 11

Test Results after 1 minute contact time

| Tube number | Example 1 Growth (+ or −) | Example 2 Growth (+ or −) |
|---|---|---|
| 1 | − | − |
| 2 | − | − |
| 3 | − | − |
| 4 | − | − |
| 5 | − | − |
| 6 | − | − |
| 7 | − | − |
| 8 | − | − |
| 9 | − | − |
| 10 | − | − |

TABLE 12

Test Results after 5 minute contact time

| Tube number | Example 1 Growth (+ or −) | Example 2 Growth (+ or −) |
|---|---|---|
| 1 | − | − |
| 2 | − | − |
| 3 | − | − |
| 4 | − | − |
| 5 | − | − |
| 6 | − | − |
| 7 | − | − |
| 8 | − | − |
| 9 | − | − |
| 10 | − | − |

TABLE 13

Test Results after 10 minute contact time

| Tube number | Example 1 Growth (+ or −) | Example 2 Growth (+ or −) |
|---|---|---|
| 1 | − | − |
| 2 | − | − |
| 3 | − | − |
| 4 | − | − |
| 5 | − | − |
| 6 | − | − |
| 7 | − | − |
| 8 | − | − |
| 9 | − | − |
| 10 | − | − |

TABLE 14

| control | |
|---|---|
| Sample | Growth (= or −) |
| *Pseudomonas aeruginosa* positive control 1 | + |
| *Pseudomonas aeruginosa* positive control 2 | + |
| Media Control 1 | − |
| Media Control 2 | − |

TABLE 15

| Bacteriostasis controls | |
|---|---|
| Tube | Growth (+ or −) |
| Spray 1, 1-min Tube 1 | + |
| Spray 1, 5-min Tube 1 | + |
| Spray 1, 10-min Tube 1 | + |
| Spray 2, 1-min Tube 1 | + |
| Spray 2, 5-min Tube 1 | + |
| Spray 2, 10-min Tube 1 | + |

All controls produced the expected results. The positive control slides that were not treated with disinfectant showed characteristic growth for *Pseudomonas aeruginosa*. The media control tube with no slide showed no growth. The re-inoculated bacteriostasis control tubes all showed positive growth upon re-incubation, indicating no bacteriostasis from the residual disinfectant left on the slides.

The two-part systems of Example 1 and 2 were able to completely kill the dried organisms on all of the slides for all of the time points. Since killing of ten out of ten slides is a required to pass the AOAC Germicidal Spray test, the systems passed the test at the 1, 5, and 10 minutes contact times.

Example 6

Kill-Time Studies of Methicillin-Resistant *Staphylococcus aureus* (MRSA) Using Disinfectants of Example 2

A study was conducted to determine the antimicrobial activity of the disinfectant system of Example 2 when challenged with an organic load, on the test organism Methicillin-resistant *Staphylococcus aureus* (MRSA). This was accomplished by performing a standard AOAC Germicidal Spray Product as Disinfectants Protocol; Method 961.02 using test organisms dried onto glass slides which were sprayed 3 seconds and held for 1, 5, and 10 minutes prior to subculture.

Specifically, the test suspension was prepared by growing a culture of Methicillin-resistant *Staphylococcus aureus* (MRSA), ATCC 43301, in Nutrient Broth at 37° C., for 48 hour. A 10 µaliquot of the test culture was transferred to 1"×1" square glass slides in Petri dishes using a calibrated micropipette. The inoculum was immediately spread evenly over the entire surface of the slide. The dish was covered, and the process was repeated until 10 slides per time point were inoculated.

The slides were then dried in a 37° C. incubator for 30-40 minutes. The slides with MRSA, 10 per Example 2 per time period (60 total), were sprayed with the test disinfectant using the system of Example 2. The slides were sprayed for 3 seconds at a distance of about 6-8 inches from the slides. The slides were held for 1, 5, and 10 minutes, and then excess liquid was drained from the slides. The slides were then transferred to individual 32×200 mm glass culture tubes containing 20 ml Fluid Thioglycollate broth and shaken thoroughly. All of the tubes were incubated at 37° C. for 48 hours. The tubes were then observed for growth (+) or no growth (−) by visual turbidity.

As a control two inoculated, but unsprayed slides prepared as described above were used. A media control containing no slide was also included. To check for bacteriostasis, a few representative negative subculture tubes are evaluated for residual disinfectant bacteriostasis by inoculating each with a small look contaminated with a respective test culture suspension and re-incubating the tubes at 37° C. for 24 hours.

The results of the test are provided as follows:

TABLE 16

Test Results after 1 minute contact time

| Tube number | Example 2 Growth (+ or −) |
|---|---|
| 1 | − |
| 2 | − |
| 3 | − |
| 4 | − |
| 5 | − |
| 6 | − |
| 7 | − |
| 8 | − |
| 9 | − |
| 10 | − |

TABLE 17

Test Results after 5 minute contact time

| Tube number | Example 2 Growth (+ or −) |
|---|---|
| 1 | − |
| 2 | − |
| 3 | − |
| 4 | − |
| 5 | − |
| 6 | − |
| 7 | − |
| 8 | − |
| 9 | − |
| 10 | − |

TABLE 18

Test Results after 10 minute contact time

| Tube number | Example 2 Growth (+ or −) |
|---|---|
| 1 | − |
| 2 | − |
| 3 | − |
| 4 | − |
| 5 | − |
| 6 | − |
| 7 | − |
| 8 | − |
| 9 | − |
| 10 | − |

TABLE 19 control

| Sample | Growth (= or −) |
|---|---|
| MRSA positive control 1 | + |
| MRSA positive control 2 | + |
| Media Control 1 | − |

TABLE 20

Bacteriostasis controls

| Tube | Growth (+ or −) |
|---|---|
| Spray 2, 1-min Tube 1 | + |
| Spray 2, 5-min Tube 1 | + |
| Spray 2, 10-min Tube 1 | + |

All controls produced the expected results. The positive control slides that were not treated with disinfectant showed characteristic growth for MRSA. The media control tube with no slide showed no growth. The re-inoculated bacteriostasis control tubes all showed positive growth upon re-incubation, indicating no bacteriostasis from the residual disinfectant left on the slides.

The two-part system of Example 2 was able to completely kill the dried organisms on all of the slides for all of the time points. Since killing of ten out of ten slides is a required to pass the AOAC Germicidal Spray test, the systems passed the test at the 1, 5, and 10 minutes contact times.

Example 7

Preparation of Disinfectant System

An aqueous disinfectant system is prepared in accordance with embodiments of the present disclosure, which includes the following ingredients in approximate amounts:
First solution:
10 wt % acetic acid
0.05% polyvinyl alcohol
Balance 200 ppm silver colloids in water
Second solution:
7 wt % magnesium peroxide in water
The first solution and the second solution were each placed in separate chambers from which they could be withdrawn and mixed through a dispenser.

Example 8

Preparation of Disinfectant System

An aqueous disinfectant system is prepared in accordance with embodiments of the present disclosure, which includes the following ingredients in approximate amounts:
First solution:
8 wt % citric acid
2% polyvinyl alcohol
Balance 300 ppm silver colloid in water
Second solution:
5 wt % sodium percarbonate in water
The first solution and the second solution were each placed in separate chambers from which they could be withdrawn and mixed through a dispenser.

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

What is claimed is:

1. A disinfectant system comprising:
a dispenser;
a first chamber in fluid communication with the dispenser, the first chamber containing a first aqueous solution comprising (A) polyvinyl alcohol, (B) 3% to about 20% by weight of an organic carboxylic acid selected from the group consisting of citric acid, acetic acid, formic acid, oxalic acid, propanoic acid, lactic acid, butanoic acid, pentanoic acid, hexanoic acid, adipic acid, benzoic acid, and combinations thereof, and (C) 10 ppm to about 1,000 ppm by weight colloidal transition metal particles selected from the group consisting of colloidal silver metal particles, colloidal silver alloy particles, and combinations thereof; and
a second chamber in fluid communication with the dispenser, the second chamber containing a second aqueous solution comprising 0.5% to about 10% by weight of an activator selected from the group consisting of hydrogen peroxide, methyl ethyl ketone peroxide, carbamide peroxide, potassium superoxide, lithium peroxide, barium peroxide, sodium peroxide, calcium peroxide, strontium peroxide, magnesium peroxide, sodium percarbonate, sodium peroxide, potassium peroxide, and combinations thereof.

2. The system of claim 1, wherein the system is substantially free of chlorine and bromine-containing components.

3. The system of claim 1, wherein the system is substantially free of iodophore-containing components.

4. The system of claim 1, wherein the system is substantially free of phenolic-containing components.

5. The system of claim 1, wherein the system is substantially free of quaternary ammonium-containing components.

6. The system of claim 1, wherein the concentration of polyvinyl alcohol is 0.05% to 10% by weight of the first aqueous solution.

7. The system of claim 1, wherein the concentration of polyvinyl alcohol is 0.1% to 5% by weight of the first aqueous solution.

8. The system of claim 1, wherein the concentration of polyvinyl alcohol is 0.1% to 1% by weight of the first aqueous solution.

9. The system of claim 1, wherein the concentration of the colloidal transition metal particles is 10 ppm to 300 ppm by weight of the first aqueous solution.

10. The system of claim 1, wherein the colloidal transition metal particles are colloidal silver metal particles.

11. The system of claim 1, wherein the organic carboxylic acid is citric acid.

12. The system of claim 1, wherein the organic carboxylic acid is acetic acid.

13. The system of claim 1, wherein the concentration of the organic carboxylic acid is 5% to about 15% by weight of the first aqueous solution.

14. The system of claim 1, wherein the concentration of the organic carboxylic acid is 7% to about 13% by weight of the first aqueous solution.

15. The system of claim 1, wherein the activator is hydrogen peroxide.

16. The system of claim 1, wherein the first aqueous solution is pressurized.

17. The system of claim 1, wherein the second aqueous solution is pressurized.

18. The system of claim 16, wherein the second aqueous solution is pressurized.

* * * * *